United States Patent [19]

Flury

[11] Patent Number: 5,072,014
[45] Date of Patent: Dec. 10, 1991

[54] CYCLIC PHOSPHATES AND THIOPHOSPHATES USEFUL AS FLAME RETARDANTS FOR HALOGEN-FREE POLYMERS

[75] Inventor: Peter Flury, Himmelried, Switzerland

[73] Assignee: Ciba-Geigy Corporation, Ardsley, N.Y.

[21] Appl. No.: 559,464

[22] Filed: Jul. 30, 1990

[30] Foreign Application Priority Data

Aug. 9, 1989 [CH] Switzerland .................. 2923/89

[51] Int. Cl.$^5$ .......................................... C07F 9/6574
[52] U.S. Cl. .................................................. 558/86
[58] Field of Search .................................. 558/86, 79

[56] References Cited

U.S. PATENT DOCUMENTS 3,297,631  1/1967  Bown et al. ........................ 558/86

Primary Examiner—Mary C. Lee
Assistant Examiner—Michael G. Ambrose
Attorney, Agent, or Firm—Luther A. R. Hall

[57] ABSTRACT

Compounds of the general formula

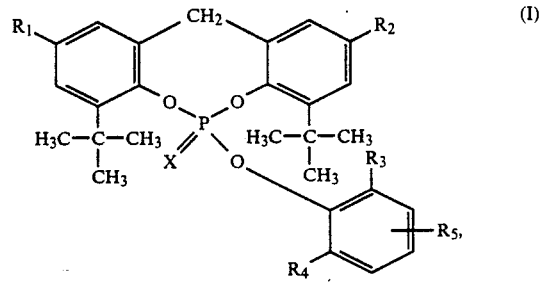

wherein $R_1$ and $R_2$ are each independently of the other hydrogen, $C_1$–$C_6$alkyl, or phenyl or naphthyl, each unsubstituted or substituted by 1 to 3 $C_1$–$C_4$alkyl groups, $R_3$ and $R_4$ are each independently of the other hydrogen or $C_1$–$C_4$alkyl, with the proviso that $R_3$ and $R_4$ may not simultaneously be hydrogen, and $R_5$ is hydrogen, $C_1$–$C_6$alkyl, or phenyl or naphthyl, each unsubstituted or substituted by 1 to 3 $C_1$–$C_4$alkyl groups, and X is oxygen or sulfur, are very suitable flame retardants for polymers.

10 Claims, No Drawings

CYCLIC PHOSPHATES AND THIOPHOSPHATES USEFUL AS FLAME RETARDANTS FOR HALOGEN-FREE POLYMERS

The present invention relates to novel phosphorus compounds, to halogen-free polymers containing them, and to the use of said novel phosphorus compounds as flame retardants for halogen-free polymers.

Polymers are commonly made more flame-resistant by reducing the organic and hence flammable component, for example by adding fillers which are nonflammable or of low flammability, for example quartz flour, glass, wollastonite and the like. However, the amount of filler added must be substantial in order to ensure adequate flame-resistance, with the consequence that insoluble problems often arise during the preparation and processing of the reaction resin compositions.

Another possibility is the addition of flame retardants to the polymers. Suitable flame retardants are inorganic compounds such as boron compounds or metal hydroxides. In this case too it is necessary to add large amounts of such modifiers, again with adverse consequences for the preparation and processing of the polymers. The use of halogenated compounds such as brominated bisphenol A or decabromodiphenyl ether, for example in laminating and encapsulating resins, has the serious drawback that, in the event of fire, hydrogen halide is set free. This circumstance poses not only toxicological problems, but also constitutes an extremely high risk of corrosion which, in the event of fire in an electrical and, in particular electronic, system can lead to serious secondary damage resulting from electrochemical corrosion.

The disposal of such polymers too is environmentally hazardous, as there is the potential danger of the formation of highly toxic (dioxin-type) products.

Halogenated phosphoric acid esters are disclosed as flame retardant additives for plastics materials in U.S. Pat. No. 3,689,602.

The use of flame retardant organophosphorus compounds which are not incorporated in the polymers results in a kind of plasticising effect, which leads to a substantial loss of mechanical and electrical properties of the polymers so treated. For example, the mechanical strength and glass transition temperature are reduced by the plasticising action of the organophosphorus compound. In addition, these compounds are unstable to hydrolysis, resulting in an increased water absorption of the reaction resin moulding material and simultaneous formation of different phosphorus compounds.

Halogen-free sterically hindered phosphonates are disclosed as image dye stabilisers for photographic layers in European patent application 0 265 196.

Surprisingly, it has now been found that cyclic phosphates and thiophosphates protected by voluminous groups increase the flame resistance of polymers without substantially affecting their other properties such as heat resistance, mechanical strength, dielectric constant or water absorption.

The present invention relates to compounds of the general formula I

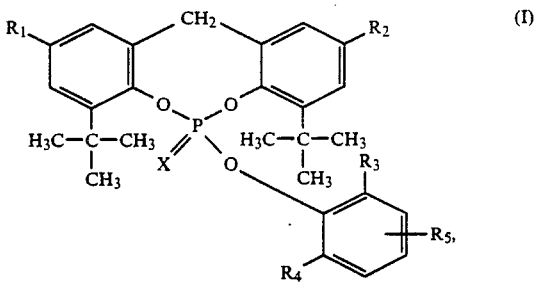

wherein $R_1$ and $R_2$ are each independently of the other hydrogen, $C_1$–$C_6$alkyl, or phenyl or naphthyl, each unsubstituted or substituted by 1 to 3 $C_1$–$C_4$alkyl groups, $R_3$ and $R_4$ are each independently of the other hydrogen or $C_1$–$C_4$alkyl, with the proviso that $R_3$ and $R_4$ may not simultaneously be hydrogen, and $R_5$ is hydrogen, $C_1$–$C_6$alkyl, or phenyl or naphthyl, each unsubstituted or substituted by 1 to 3 $C_1$–$C_4$alkyl groups, and X is oxygen or sulfur.

$R_1$, $R_2$ and $R_5$ as $C_1$–$C_6$alkyl and $R_3$ and $R_4$ as $C_1$–$C_4$alkyl may be straight chain and branched alkyl groups such as methyl, ethyl, n-propyl, isopropyl, n-butyl, isobutyl, sec-butyl, tert-butyl, and $R_1$, $R_2$ and $R_5$ may additionally be n-pentyl, isopentyl or n-hexyl. $R_5$ is preferably para-positioned to the ester bond.

The alkyl moiety or moieties in $R_1$, $R_2$ and $R_5$ as phenyl or naphthyl which are substituted by 1 to 3 $C_1$–$C_4$alkyl groups are the same $C_1$–$C_4$alkyl groups as defined above for $R_3$ and $R_4$. These substituents may be in any of the possible positions. Monosubstitution is preferred, especially in para-position for phenyl and in 6- or 7-position for naphthyl.

Preferred compounds of formula I are those wherein $R_1$ and $R_2$ are each independently of the other hydrogen or $C_1$–$C_6$alkyl, more particularly hydrogen, methyl or ethyl. $R_1$, $R_2$ preferably have the same meaning.

In a further preferred embodiment, $R_3$ and $R_4$ in the compounds of formula I have the same meaning and are methyl or ethyl, preferably methyl.

Interesting compounds of formula I are also those wherein $R_3$ is hydrogen and $R_4$ is isopropyl or tert-butyl.

Yet a further embodiment of the invention relates to compounds of formula I, wherein $R_5$ is hydrogen or $C_1$–$C_4$alkyl, preferably hydrogen or methyl.

Particularly interesting compounds of formula I are those wherein X is sulfur.

Of very particular interest are compounds of formula I wherein $R_1$ and $R_2$ are methyl, $R_3$ is hydrogen or methyl, $R_4$ is methyl or tert-butyl and $R_5$ is hydrogen or methyl.

The compounds of formula I are prepared in a manner which is known per se.

The compounds of formula I, wherein X is oxygen, may be prepared as described in European patent application 0 265 196 by reacting a bisphenol of formula

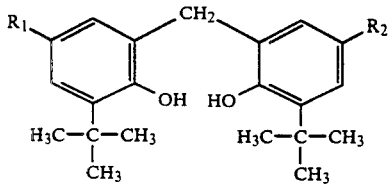
(II)

with a phosphorus acid dichloride of formula III

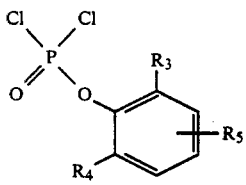
(III)

The phosphorus acid dichloride of formula III is prepared, for example, by reacting the phenol of formula IV

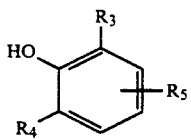
(IV)

with POCl₃.

A further route of synthesis is the stepwise reaction of a bisphenol of formula II with POCl₃ to the corresponding phosphorus acid dichloride V

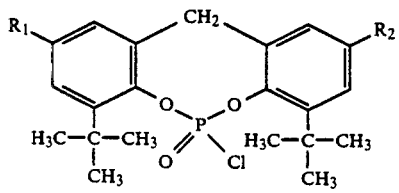
(V)

which is subsequently reacted with a phenol of formula IV to the compound of formula I.

The reactions are conveniently carried out at room temperature or at elevated temperature in an inert solvent such as toluene, in the presence of a base such as triethylamine or pyridine.

The compounds of formula I, wherein X is sulfur, may be prepared by reacting a bisphenol of formula II with PCl₃ to the corresponding phosphorous acid chloride, which is then reacted with a phenol of formula IV to the phosphite of formula VI

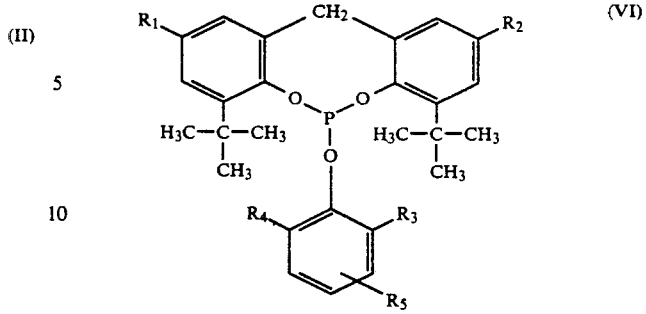
(VI)

which is subsequently in turn converted into the compound of formula I, wherein X is sulfur, by reaction with elemental sulfur in a manner known per se (q.v. Houben-Weyl "Methoden der Org. Chemie," Vol. 12/2, page 647).

The compounds of formula I, wherein X is oxygen, may also of course be prepared by oxidation of the compounds of formula VI, for example with peracetic acid and the like.

The compounds of formula I are preeminently suitable for use as flame retardants for polymers, especially for halogen-free polymers.

The amount of compound of formula I added to the polymer as a flame retardant may be varied over a wide range. Usually from 0.1 to 100 parts by weight are used per 100 parts by weight of polymer. Preferably 0.5 to 30 parts are used and, most preferably, from 2 to 20 parts by weight per 100 parts by weight of polymer. The optimum amount used depends on the nature of the polymer and the nature of the compound of formula I and may be readily determined by simple experiment. However, because the compounds of formula I are generally effective at low levels of addition and are furthermore halogen-free, they produce less unwanted effects in the polymer than other known flame retardant additives.

The compounds of formula I may be used in various physical forms depending on the polymer used and the desired properties. For instance they may be ground to a finely divided form to enable better dispersion throughout the polymer. If desired, mixtures of different compounds of formula I may also be used.

The compounds of formula I may be used in various polymers.

Examples of polymers which may be rendered flame retardent are:

1. Polyphenylene oxides and sulfides, and blends of these polymers with polystyrene graft polymers or styrene copolymers such as high impact polystyrene, EPDM copolymers with rubbers, as well as blends of polyphenylene oxide with polyamides and polyesters.

2. Polyurethanes which are derived from polyethers, polyesters or polybutadiene with terminal hydroxyl groups on the one hand and aliphatic or aromatic polyisocyanates on the other hand including polyisocyanurates, as well as precursors thereof.

3. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide or poly-m-phenylene iso-phthalamide, as well as copolymers thereof with polyethers, such as with polyethylene glycol, polypropylene glycol or polytetramethylene glycols.

4. Polyesters which are derived from dicarboxylic acids and di-alcohols and/or from hydroxycarboxylic acids or the corresponding lactones, such as polyethylene terephthalate, polybutylene terephthalate, poly-1,4-dimethylol-cyclohexane terephthalate and polyhydroxybenzoates as well as block-copolyether-esters derived from polyethers having hydroxyl end groups.

5. Unsaturated polyester resins which are derived from copolyesters of saturated and unsaturated dicarboxylic acids with polyhydric alcohols and vinyl compounds as cross-linking agents.

6. Polystyrene.

7. Graft copolymers of styrene, for example styrene on polybutadiene, styrene and acrylonitrile on polybutadiene, styrene and alkyl acrylates or methacrylates on polybutadiene, styrene and acrylonitrile on ethylene-/propylene/diene terpolymers, styrene and acrylonitrile on polyacrylates or polymethacrylates, styrene and acrylonitrile on acrylate/butadiene copolymers, as well as mixtures thereof with random copolymers of styrene or α-methylstyrene with dienes or acrylic derivatives, for instance the terpolymers of styrene known as ABS, MBS, ASA or AES terpolymers.

8. Cross-linked epoxy resins which are derived from polyepoxides, for example, from bis-glycidyl ethers, especially bisphenol A diglycidyl ethers, or from cycloaliphatic diepoxides.

9. Polycarbonates.

The crosslinked epoxy resins are particularly suitable.

Hence the present invention also relates to compositions containing a halogen-free polymer and, as flame retardant modifier, at least one compound of formula I.

The compositions of the invention may also contain other conventional ingredients, such as heat stabilisers, light stabilisers, ultra-violet light absorbers, anti-oxidants, anti-static agents, preservatives, adhesion promoters, fillers, pigments, lubricants, blowing agents, fungicides, plasticisers, processing aids, other fire-retardant additives and smoke suppressants.

Other fire retardant additives which may be used with the compounds of formula I include phosphorus containing salts such as ammonium polyphosphate, antimony oxide, hydrated alumina, bismuth oxide, molybdenum oxide, or mixtures of these compounds with zinc and/or magnesium oxide or salts.

The invention is illustrated in more detail by the following Examples.

EXAMPLE 1

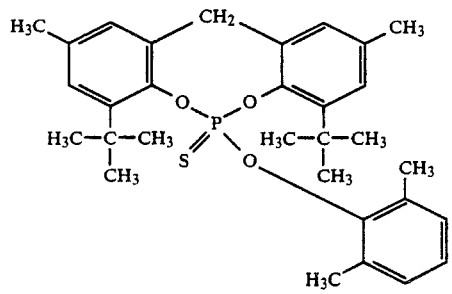

1st Step

An apparatus comprising a 2.5 l sulfonating flask, an oil bath, a thermometer, a condenser and a drying tube is charged with 137.0 g (1.0 mol) of phosphorus trichloride and 500 ml of toluene. A solution of 340.5 g (1 mol) of 2,2'-methylenebis(4-methyl-6-tert-butylphenol) and 264.0 g (3.3 mol) of pyridine in 200 ml of toluene is then added dropwise at room temperature. The batch is then stirred under reflux and a solution of 130.0 g of 2,6-dimethylphenol in 330 ml of toluene is subsequently added rapidly. The reaction mixture is stirred for 10 hours under reflux, cooled, and poured into 1.2 liters of water. The organic phase is separated, washed with dilute HCl and dilute NaHCO₃ solution, dried over sodium sulfate, and concentrated by evaporation on a rotary evaporator. The residue is recrystallised from isopropanol, affording 390 g (80% of theory) of colourless crystals (m.p. 139° C.) of the intermediate of the structure (1)

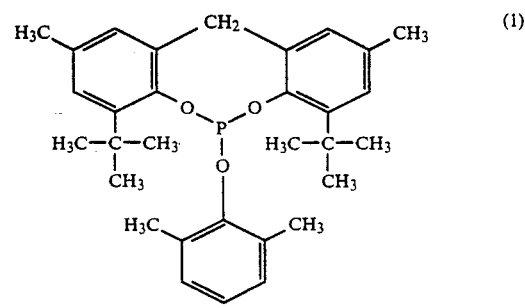

¹H-NMR: (CDCl₃): 1.2 (s, 18 H, tert-butyl); 2,3 (s, 6 H, CH₃); 2.5 (s, 6 H, CH₃); 3.3–4.5 (m, 2 H, —CH₂—); 7.0–7.2 (m, 7 H, aryl).

$C_{31}H_{39}O_3P$: cal.: C: 75.8%; H: 7.9%; P: 6.3%. (462.6): found: C: 75.8%; H: 7.9%; P: 6.4%.

2nd Step

An apparatus comprising a 750 ml sulfonating flask, a thermometer and an oil bath is charged with 269.0 g (0.548 mol) of the intermediate of structure (1) and 19.3 g (0.603 mol) of sulfur, and the mixture is heated for 3 hours to 180° C. The reaction mixture is thereafter cooled and recrystallised from a mixture of methyl ethyl ketone/ethanol, affording 235 g (82% of theory) of colourless crystals which melt at 168° C.

¹H-NMR: (CDCl₃): 1.25 (s, 18 H, tert-butyl); 2.3 (s, 6 H, CH₃); 2.5 (s, 6 H, CH₃); 3.4–4.5 (m, 2 H, —CH₂—); 7.0 (s, br, 7 H, aryl).

$C_{31}H_{39}O_3PS$: cal.: C: 71.24%; H: 7.52%; S: 6.13% P: 5.93%. (522.68): found: C: 10.90%; H: 7.60%; S: 6.30% P: 6.10%.

EXAMPLE 2

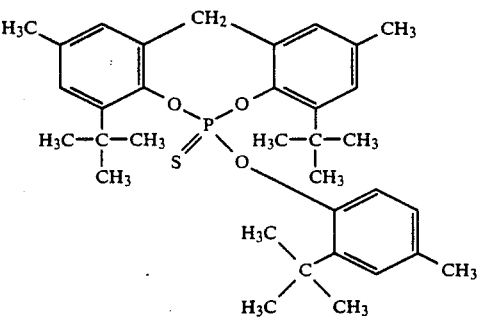

1st Step

In accordance with the procedure of Example 1, step 1, the intermediate of structure (2) is prepared using 2-tert-butyl-4-methylphenol in place of 2,6-dimethylphenol.

The reaction mixture is recrystallised from isopropanol, to give 78% of theory of colourless crystals of the intermediate of structure (2) which melt at 200 m.p.

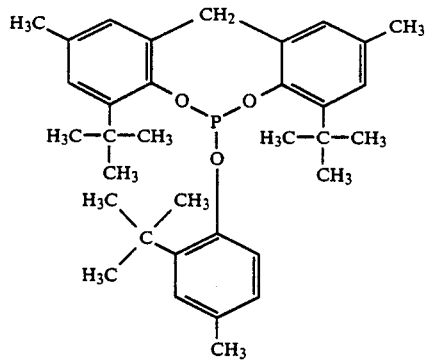

(2)

¹H-NMR: (CDCl): 1.3 (s, 18 H, tert-butyl); 1.5 (s, 9 H, tert-butyl); 2.3 (s, br, 9 H, CH₃); 3.4–4.5 (m, 2 H, —CH₂—); 6.9–7.6 (m, 7 H, aryl).

C₃₄H₄₅O₃P: cal.: C: 76.7%; H: 8.5%; P: 5.8%. (462.6): found: C: 76.8%; H: 8.6%; P: 5.8%.

2nd Step

An apparatus comprising a 750 ml sulfonation flask, a thermometer, a condenser, an oil bath and a drying tube is charged with 266.4 g (0.50 mol) of the intermediate of structure (2), 16.8 g (0.525 mol) of sulfur and 70 ml of decalin, and the mixture is heated on the oil bath for 3 hours to 200° C. The reaction mixture is then cooled to 100° C. and 150 ml of methyl ethyl ketone are added. 100 ml of ethanol are then added dropwise to this solution and the batch is cooled to room temperature. The colourless precipitate which forms is isolated by filtration, washed with ethanol and dried under vacuum, affording 267 g (94% of theory) of product with a melting point of 215° C.

¹H-NMR: (CDCl₃): 1.3 (s, 18 H, tert-butyl); 1.45 (s, 9 H, tert-butyl); 2.3 (s, 6 H, CH₃); 6.95–7.80 (m, 7 H, aryl).

C₃₄H₄₅O₃PS: cal.: C: 72.3%; H: 8.0%; P: 5.5% S: 5.7%. (564.77): found: C: 72.2%; H: 8.0%; P: 5.5% S: 5.8%.

EXAMPLE 3

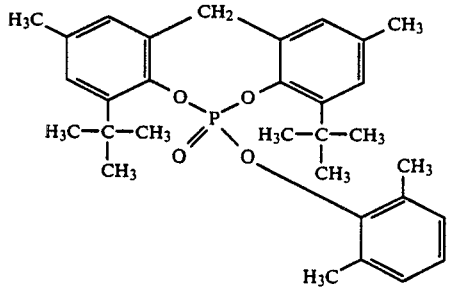

An apparatus comprising a 2.5l sulfonation flask, a thermometer, a condenser, an oil bath and a drying tube is charged with 153.3 g (1.0 mol) of phosphoroxy chloride and 400 ml of xylene. A solution of 122.2 g of 2,6-dimethylphenol and 396.0 g (5.0 mol) of pyridine in 175 ml of xylene is then added dropwise at room temperature over ca. 30 minutes. The reaction mixture is stirred for 1 hour under reflux and then a solution of 340.5 g (1.0 mol) of 2,2'-methylenebis(4-methyl-6-tert-butylphenol) and 79.2 g (1.0 mol) of pyridine in 250 ml of xylene is added rapidly. The reaction mixture is stirred for 40 hours under reflux, cooled, and poured into 1.4l of water. The organic phase is separated, washed with dilute HCl and dilute NaHCO₃ solution, dried over sodium sulfate, and concentrated by evaporation on a rotary evaporator. The residue is crystallised from ethanol, affording 408 g (81% of theory) of colourless crystals of m.p. 159° C.

¹H-NMR: (CDCl₃): 1.2 (s, 18 H, tert-butyl groups); 2.3 (s, 6 H, CH₃); 3.5–4.5 (m, 2 H, —CH₂—); 7.5 (s, br, 7 H, aryl).

C₃₁H₃₉O₄P: cal.: C: 73.49%; H: 7.76%; P: 6.11%. (506.62): found: C: 73.61%; H: 7.78%; P: 5.96%.

EXAMPLE 4

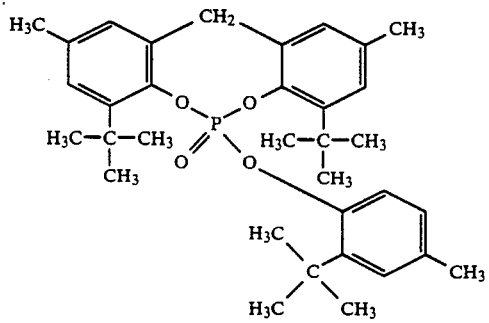

The above compound is prepared as described in Example 3 using 2-tert-butyl-4-methylphenol in place of 2,6-dimethylphenol.

The reaction mixture is rcrystallised from toluene, affording 416 g (76% of theory) of colourless crystals which melt at 224° C.

¹H-NMR: (CDCl₃): 1.3 (s, 18 H, tert-butyl); 1.45 (s, 9 H, tert-butyl); 2.3 (s, 6 H, CH₃); 2.35 (s, 3 H, CH₃); 3.7–4.4 (m, 2 H, —CH₂—); 6.95–7.70 (m, 7 H, aryl).

C₃₄H₄₅O₄P: cal.: C: 74.4%; H: 8.3%; P: 5.6%. (548.70): found: C: 74.3%; H: 8.4%; P: 5.7%.

EXAMPLE 5

Test specimens (4 mm sheets) are prepared from the following epoxy resin to which flame retardants of Examples of 1 to 4 added:

100 parts by weight of bisphenol A diglycidyl ether (epoxy value 5.6 eq/kg)

10 parts by weight of a mixture of 25 parts by weight of dicyandiamide and 75 parts by weight of oligomeric cyanoguanidine (from EP 0 306 451, Ex. 3)

0.3 part by weight of 2-methylimidazole 15 parts by weight of flame retardant.

The specimens are cured for 1 hour at 160° C. and for 2 hours at 180° C. to give a yellowish clear epoxy resin.

After removal from the mould, the specimens are tested for their flammability in accordance with the standard of Underwriters Laboratories Inc. UCL 94, third edition (revised) of Sept. 25, 1981 (horizontal burn test).

In addition, the glass transition temperature is determined by the DSC method (differential scanning calorimetry). The boiling water and cold water absorption are also determined.

A thermogravimetric analysis is also carried out, in which the temperature is determined at which the specimen exhibits a weight loss of 5 and 10% respectively.

The results are summarised in Table 1.

TABLE 1

| Flame retardant according to Example | — | 1 | 2 | 3 | 4 |
|---|---|---|---|---|---|
| flame inhibition according to UL at 4 mm | burns | V-O | V-O | V-O | V-O |
| glass transition temperature (DSC) [°C.] | 150 | 138 | 140 | 141 | 145 |
| boiling water absorption (4 mm/1 h) [% by weight] | 0.39 | 0.29 | 0.42 | 0.40 | 0.38 |
| cold water absorption (4 mm/4 days) [% by weight] | 0.43 | | | 0.35 | 0.40 |
| thermogravimetric analysis | | | | | |
| t (−5% by weight) [°C.] | 325 | 270 | 280 | 290 | 300 |
| t (−10% by weight) [°C.] | 345 | 300 | 305 | 310 | 315 |

What is claimed is:

1. A compound of the general formula

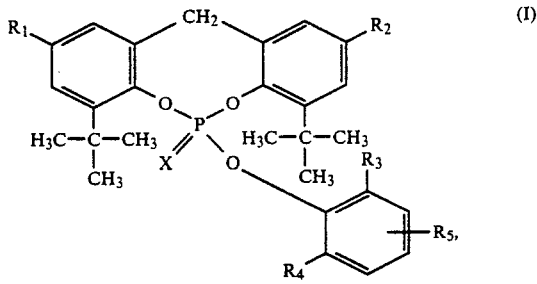

wherein $R_1$ and $R_2$ are each independently of the other hydrogen, $C_1$–$C_6$alkyl, or phenyl or naphthyl, each unsubstituted or substituted by 1 to 3 $C_1$–$C_4$alkyl groups, $R_3$ and $R_4$ are each independently of the other hydrogen or $C_1$–$C_4$alkyl, with the proviso that $R_3$ and $R_4$ may not simultaneously be hydrogen, and $R_5$ is hydrogen, $C_1$–$C_6$alkyl, or phenyl or naphthyl, each unsubstituted or substituted by 1 to 3 $C_1$–$C_4$alkyl groups, and X is oxygen or sulfur.

2. A compound according to claim 1, wherein $R_1$ and $R_2$ are each independently of the other hydrogen or $C_1$–$C_6$alkyl.

3. A compound according to claim 1, wherein $R_3$ and $R_4$ are identical and are methyl or ethyl.

4. A compound according to claim 1, wherein $R_3$ is hydrogen and $R_4$ is isopropyl or tert-butyl.

5. A compound according to claim 2, wherein $R_1$ and $R_2$ are identical.

6. A compound according to claim 5, wherein $R_1$ and $R_2$ are hydrogen, methyl or ethyl.

7. A compound according to claim 3, wherein $R_3$ and $R_4$ are methyl.

8. A compound according to claim 1, wherein $R_5$ is hydrogen or $C_1$–$C_4$alkyl.

9. A compound according to claim 1, wherein $R_1$ and $R_2$ are methyl, $R_3$ is hydrogen or methyl, $R_4$ is methyl or tert-butyl and $R_5$ is hydrogen or methyl.

10. A compound according to claim 1, wherein X is sulfur.

* * * * *